United States Patent [19]

Pungor et al.

[11] 4,021,325
[45] May 3, 1977

[54] SELECTIVE FLUORIDE-SENSITIVE ELECTRODE

[75] Inventors: Ernö Pungor; Elek Doktor; Márton Patkó; Jenö Havas; Lajos Kecskés, all of Budapest, Hungary

[73] Assignee: Elektrokemiai Muszergyarto Szov., Budapest, Hungary

[22] Filed: July 7, 1975

[21] Appl. No.: 593,567

[30] Foreign Application Priority Data

Oct. 31, 1974 Hungary .............................. RA-623

[52] U.S. Cl. ........................... 204/195 M; 29/592; 204/1 T
[51] Int. Cl.² .................. G01N 27/30; G01N 27/50
[58] Field of Search .......... 204/195 M, 1 B; 29/592

[56] References Cited

UNITED STATES PATENTS

| | | | |
|---|---|---|---|
| 3,431,182 | 3/1969 | Frant | 204/1 B |
| 3,607,710 | 9/1971 | Farren | 204/195 M |
| 3,822,198 | 7/1974 | Bauke | 204/195 M |
| 3,892,833 | 7/1975 | Hattori et al. | 204/195 M X |

FOREIGN PATENTS OR APPLICATIONS 343,211  7/1972  U.S.S.R. ....................... 204/195 M

Primary Examiner—G. L. Kaplan

[57] ABSTRACT

A selective fluoride-sensitive electrode featuring a sensor block of spherical surface compensating the effect of thermodilatation and prepared from the fluorides of a lanthanide mixture corresponding to the composition of the natural occurrents or from a mixture composed of the majority of lanthanides.

3 Claims, 2 Drawing Figures

SELECTIVE FLUORIDE-SENSITIVE ELECTRODE

The invention relates to a highly sensitive, selective fluoride-sensitive electrode, featuring a sensor block of spherical surface compensating the effect of thermal dilatation; further to a process for the preparation thereof.

The development of measuring electrodes capable of rapid, highly sensitive and continuous determination of the concentration of fluoride ions is a requirement urgently needed in connection with the measurement of water and air pollution. Similar requirements are encountered by those working in the field of water analysis, further in the analysis of feedstuffs, cosmetics, biological materials and fluids, etc.

From among the known methods, one of the fastest and most sensitive one is the potentiometric measuring technique. The essence of the latter is that a fluoride-sensitive electrode is placed into the solution to be tested and conclusions are drawn on the fluoride ion concentration of the solution on the basis of the magnitude of the potential developed at the electrode.

Up to now, there are two patents known, on the basis of which fluoride-sensitive electrodes can be produced. The first of these deals with the preparation of heterogenous membranes and membrane electrodes (Hungarian Pat. No. 152,106, 1963; the same in the U.S.: U.S. Pat. No. 3,446,726; in England: B Pat. No. 1,079,988; in France: French Pat. No. 1,402,343; in Italy: Italian Pat. No. 732,329; in Sveden: Swedish Pat. No. 323,537; in Switzerland: Swiss Pat. No. 472,674; in Austria: Austrian Pat. No. 268,204; in Japan: Japanese Pat. No. 497,044) whereas the second with homogeneous membrane electrodes (B.P. 1,131,574; 1967).

Heterogeneous membrane electrodes are prepared in such a manner that a salt sparingly soluble in a given solvent, e.g. water, a so-called precipitate - in the case of a fluoride-sensitive electrode, for example a precipitate of lanthanum-fluoride - is homogenized in a silicone rubber monomer and the homogenizate is cured after having formed a membrane therefrom. A portion of the rubber membrane, containing the precipitate as a filler, is secured - as a sensor - to the end of a tube; an electrolyte is placed into the tube and a potential outlet terminal is placed into the electrolyte.

Homogeneous membrane electrodes are prepared in such a manner that the precipitate (in the case of the patent mentioned: lead fluoride, the trifluoride of bismuth, scandium, yttrium, or one of the lanthanides, or else a mixture of the trifluorides of cerium, lanthanum, praseodymium, neodymium) is compressed to a membrane or formed to a monocrystalline wafer (membrane). The crystal membrane prepared in this manner is, as a sensor, cemented to the end of a plastic tube and, in the following, the procedure is similar to that described in connection with the heterogeneous membrane electrodes.

Electrodes produced by the known procedures do not fulfill totally the requirements set in connection with them. Fluoride-sensitive heterogeneous rubber membrane electrodes are vulnerable and are operative only for a period of a few months; the known homogeneous membrane electrodes tend to crack at the junction of the sensor crystal membrane, e.g. lanthanum fluoride crystal membrane, and the plastic electrode body and as a consequence of this they show "memory effects". (Memory is the phenomenon when the electrode delivers fluoride ions from the previous sample, bound e.g. in the cracks, into the next sample solution, whereby the concentration of the latter is altered.) This phenomenon falsifies the measured results, on the one hand, and, on the other, it considerably increases (to a three- to five-fold value) the time required to reach equilibrium potential, i.e. the response time of the electrode.

The sensitivity of the known homogeneous membrane electrodes is lower by at least one order of magnitude than that which can be reached according to our present knowledge; in addition to this, they are very expensive, their value being comparable to that of the measuring instrument connected to them.

The design of the selective fluoride-sensitive electrode according to the present invention is such that it compensates for the effect of thermal expansion, and consequently no cracks appear at the contact surface of the sensor block and the plastic electrode body and, consequently, no "memory effect" is encountered; the response time is hereby reduced to 10–20 sec.

A further result of the thermal expansion compensating property of the electrode is that the latter can be used at temperatures higher by 20° – 30° C than electrodes known up to now.

The design of the sensor of the electrode in the form of a spherical body or a block of curved surface rather than in the form of a membrane, and the treatment of the surface of the sensor block by isothermal recrystallization result in a striking new technical effect inasmuch as the solubility product of the precipitate forming the material of the specially polished, spherical-surface sensor block is lower than that of a precipitate plate of circular shape and possessing edges and spices. Consequently, the sensitivity of the electrode is increased and the lower concentration limit of the measuring range is lower by about one order of magnitude than that of the known fluoride-sensitive electrodes, i.e. the measuring range of the electrodes is increased by one order of magnitude. (As regards the connection between solubility product and lower limit of the measuring range, refeence reference made to the literature: Havas, J.: Ion-selective micro-capillary solid-state membrane electrodes, Chemical Communications of the Hungarian Academy of Sciences, 37, pp. 315–350 /1972/).

The sensitivity of the fluoride-sensitive electrode according to the present invention - already higher than that of the known ones - is further enhanced by the fact that the material of the sensor block is a mixture of precipitates whose structure is more favourable and whose solubility product is, in consequence of the chemical nature of the metallic components, lower than that of the mixtures known up to now.

Figure 1:
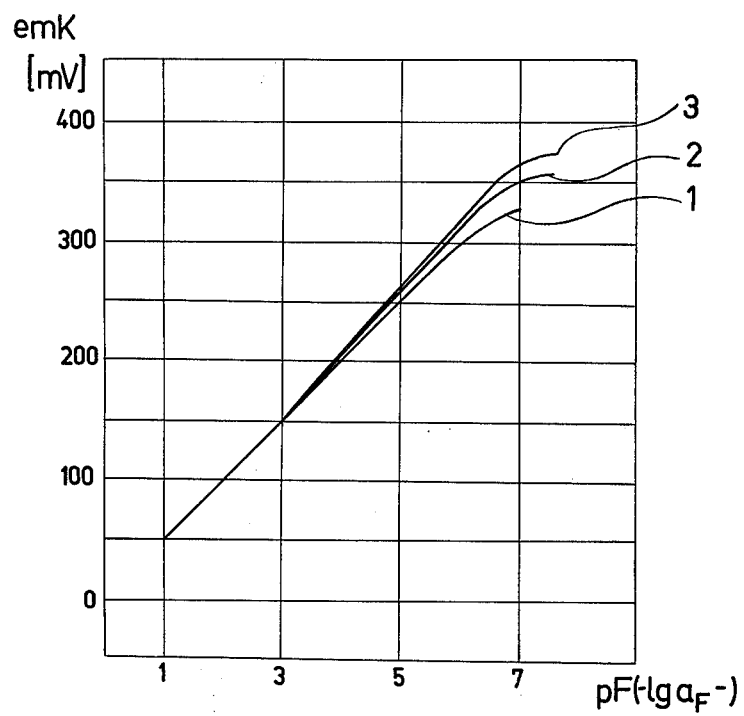
FIG. 1 is a graph of electromotive force values.

In order to support the above statement, measured results - electromotive force values, plotted against fluoride ion concentration - are shown in FIG. 1. Curve 1 shows values obtained with an electrode equipped with a circular plate-shaped sensor prepared of lanthanum and praseodymium trifluoride, Curve 2 those obtained with an electrode equipped with a spherical-surface sensor prepared of lanthanum and praseodymium fluoride, whereas Curve 3 those obtained with an electrode equipped with a spherical-surface sensor prepared of the fluorides of lanthanum, europium and dysprosium. It is apparent that the order of the lower limit of the measuring range corresponds to the order Curve 1>2>3.

The material of the sensor membrane of the known fluoride-sensitive electrodes is the trifluoride of a rare earth, or a mixture of the trifluorides of a few selected rare earths (cerium, lanthanum, praseodymium, neodymium).

As it is known, the chemical properties of the rare earths are very much alike and accordingly, the separation of the rare earths found together is a time-consuming and expensive procedure. Consequently, analytical-grade compounds of the rare earths, e.g. their trifluorides, as well as the fluoride electrodes made of them, are very expensive.

In addition to the aforesaid, it is a highly time-consuming and precision-demanding operation to prepare a lanthanide trifluoride precipitate, free of e.g. alkali ions.

The selective fluoride-sensitive electrode according to the present invention can be prepared in a manner considerably (by 50 to 70 %) more inexpensive than the known electrodes. The essence of the technique is the realization that the material of the sensor block is prepared from the fluorides of a lanthanide mixture corresponding to the composition of the natural occurrence or from a mixture composed of the majority of lanthanides. In this manner, expensive separation of the lanthanides or their preparation in analytical purity has been rendered superfluous.

As examples of the materials making up the sensor block, are those prepared from a mixture of fluoride precipitates of the metals of yttrium earth or cerium earths or metals of Group IIIB of the Periodic Table of the Elements.

An alternative example of the materials making up the sensor block is a double fluoride of metals of Group IIIB of the Periodic Table of the Elements and of sodium, potassium, or ammonium ions, preferably of the composition $XY_3F_{10}$, wherein X is sodium, potassium or ammonium and Y is a metal of Group IIIB of the Periodic Table.

Still another alternative material comprising the sensor block is a mixture of the fluorides and hydroxides or oxides of metals of Group IIIB of the Periodic Table.

In the above sensor block comprising the above-mentioned materials, it is advantageous that the block, made up of the materials is built up of a single crystal.

The design of the selective fluoride-sensitive electrode, further its preparation is, as an example, described in the following; it is understood, however, that the protection of the invention is not restricted to the Examples.

EXAMPLE 1

Figure 2:
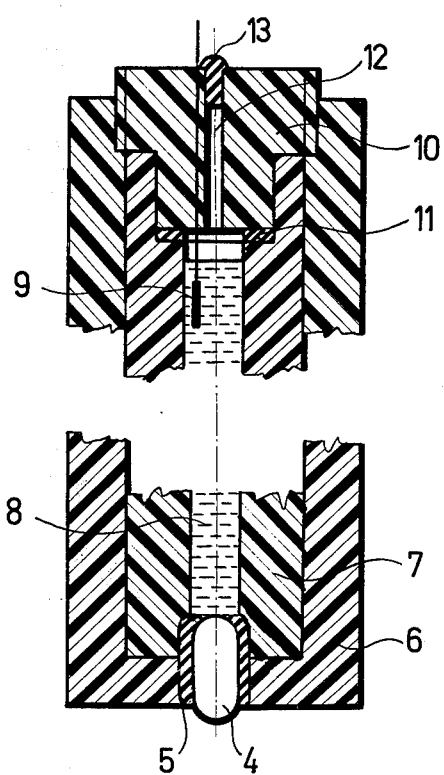
FIG. 2 is a longitudinal section, partly broken away, of the electrode.

FIG. 2 shows the structure of the fluoride-sensitive electrode in longitudinal section. Sensor block 4, composed of a mixture of ytterbium and lutetium fluorides, is in contact with an elastic insulating layer 5 - e.g. of silicone rubber - which fits into the wall portion, parallel to the surface of sensor block 4, of outer 6 and inner 7 electrode bodies made of a plastic material, e.g. PVC.

An electrolyte solution 8, containing $10^{-1}$ M sodium chloride and $10^{-1}$ M sodium fluoride is placed into the cavity of internal electrode body 7. A silver/silver chloride reference electrode 9 is immersed into electrolyte solution 8. Internal electrode body 7 is secured to external electrode body 6 by a plastic, e.g. PVC plug 10; there is a silicone rubber O-ring 11 between internal electrode body 7 and plug 10. There is an opening 12 in plug 10, covered by closure cap 13.

EXAMPLE 2

Sensor block 4 is prepared first in the following manner: a crystal, composed of the fluorides of dysprosium (0.25 %), europium (0.25 %), lanthanum (99.42 %), samarium (< 0.01 %), gadolinium (< 0.01 %), terbium < 0.01 %), holmium (< 0.01 %), erbium (< 0.01 %), thulium (< 0.01 %), ytterbium (< 0.01 %), and lutetium (< 0.01 %), is polished to the shape of a cylinder, 6 mm in dia., and of 6 mm height ending in a hemisphere 6 mm in dia. A length of 13 mm is cut from a silicone rubber tubing, five-fourths mm in dia, and placed into analytical grade petrol for a period of 10 minutes. The piece of tubing, swollen by the action of petrol, is pulled symmetrically upon sensor block 4. Sensor block 4, equipped with silicone rubber insulating layer 5, is kept at a temperature of 50° C for a period of 2 hours.

After the removal of petrol, the polyacetale external 6 and internal 7 electrode bodies are kept at a temperature of 40°–50° C for a period of 1 hour. After the elapse of 1 hour, sensor block 4, equipped with insulator layer 5 is placed into external electrode body 6 in such a manner that the longitudinal axis of sensor block 4 is parallel to the longitudinal axis of external electrode body 6.

Internal electrode body 7 is fitted into external electrode body 6, silicone rubber O-ring 11 is put into place and electrode bodies 6 and 7 are secured by polyacetale plug 10 incorporating silver/silver chloride reference electrode 9.

Solution 8, of 1M concentration with respect to both sodium fluoride and sodium chloride, is injected into the cavity of internal electrode body 7. Opening 12 is sealed by closure cap 13. The electrode thus prepared is let to stand for one day. The piece of silicone tubing protruding from external electrode body 6 is cut off. Hereupon, the end portion of the electrode containing sensor body 4 is placed into streaming distilled water of 37.0° C temperature for a period of 48–50 hours. Upon completion of the above-mentioned operation, a sensitive, selective fluoride-sensitive electrode of a surface "polished" by isothermal recrystallization is obtained.

What we claim is:
1. Selective fluoride-sensitive electrodes for the determination of fluoride ion concentrations and activities in solutions having a solid sensor built up of fluoride precipitates and an electrode body built up in such a manner that one surface portion of the sensor contacts the sample solution whereas an other surface portion of the sensor, isolated by an electrode body from the portion in contact with the sample, contacts an electrolyte solution of constant ion concentration, comprising a sensor in the form of a solid block (4), the surface portion of block (4), contacting the sample solution, being spherical or of a curved surface void of edges or spices; the surface of block (4) not contacting the sample solution or the solution of constant ion concentration (8) being connected to an elastic layer (5), which fits into the wall portion parallel to the surface at sensor block (4), of outer (6) and inner (7) tubular plastic electrode bodies, the material of the block being prepared from fluorides of a lanthanide mixture composed of the lanthanide series of rare earth metals.

2. A selective fluoride-sensitive-electrode as claimed in claim 1 wherein the block (4) is built up of a single crystal.

3. A process for the preparation of a selective fluoride-sensitive electrode described in claim 1 capable of the determination of the concentration and/or activity of fluoride ions in liquids comprising mechanical polishing and thereafter isothermal recrystallization of the surface of a block (4) covering the surface portion of said block (4) not in contact with the sample solution and the solution of constant ion concentration with an elastic layer (5), mechanically securing the rubber-covered surface portions to the wall of a tubular electrode bodies (6,7) made of plastic, filling the tubular electrode bodies (6,7) with an electrolyte solution (8) and placing a potential outlet terminal (9) into said electrolyte solution.

* * * * *